US009427006B2

(12) United States Patent
Markosyan

(10) Patent No.: US 9,427,006 B2
(45) Date of Patent: *Aug. 30, 2016

(54) HIGHLY SOLUBLE STEVIA SWEETENER

(75) Inventor: Avetik Markosyan, Yerevan (AM)

(73) Assignee: PureCircle Sdn Bhd, Kuala Lumpur (MY)

( * ) Notice: Subject to any disclaimer, the term of this patent is extended or adjusted under 35 U.S.C. 154(b) by 0 days.

This patent is subject to a terminal disclaimer.

(21) Appl. No.: 13/984,315

(22) PCT Filed: Feb. 10, 2012

(86) PCT No.: PCT/US2012/024585
§ 371 (c)(1),
(2), (4) Date: Aug. 28, 2013

(87) PCT Pub. No.: WO2012/109506
PCT Pub. Date: Aug. 16, 2012

(65) Prior Publication Data
US 2013/0330463 A1 Dec. 12, 2013

Related U.S. Application Data

(60) Provisional application No. 61/441,443, filed on Feb. 10, 2011.

(51) Int. Cl.
A23L 1/221 (2006.01)
A23L 1/236 (2006.01)
A23L 1/22 (2006.01)
A23G 3/36 (2006.01)
A23G 9/32 (2006.01)
A23L 1/308 (2006.01)
A23L 2/60 (2006.01)
A61K 8/60 (2006.01)
A61Q 19/00 (2006.01)
A61K 8/97 (2006.01)
A61K 36/28 (2006.01)
A23L 1/222 (2006.01)

(52) U.S. Cl.
CPC ............... *A23L 1/221* (2013.01); *A23G 3/36* (2013.01); *A23G 9/32* (2013.01); *A23L 1/22* (2013.01); *A23L 1/236* (2013.01); *A23L 1/2361* (2013.01); *A23L 1/2363* (2013.01); *A23L 1/2364* (2013.01); *A23L 1/2365* (2013.01); *A23L 1/2366* (2013.01); *A23L 1/2367* (2013.01); *A23L 1/308* (2013.01); *A23L 2/60* (2013.01); *A61K 8/602* (2013.01); *A61K 8/97* (2013.01); *A61K 36/28* (2013.01); *A61Q 19/00* (2013.01); *A23L 1/222* (2013.01); *A23L 1/2215* (2013.01); *A61K 2800/10* (2013.01); *A61K 2800/92* (2013.01)

(58) Field of Classification Search
USPC .......... 426/548, 615, 640, 465, 520
See application file for complete search history.

(56) References Cited

U.S. PATENT DOCUMENTS

| 3,723,410 | A | 3/1973 | Persinos |
| 4,082,858 | A | 4/1978 | Morita et al. |
| 4,171,430 | A | 10/1979 | Matsushita et al. |
| 4,219,571 | A | 8/1980 | Miyake |
| 4,361,697 | A | 11/1982 | Dobberstein et al. |
| 4,454,290 | A | 6/1984 | Dubois |
| 4,590,160 | A | 5/1986 | Nishihashi et al. |
| 4,599,403 | A | 7/1986 | Kumar |
| 4,612,942 | A | 9/1986 | Dobberstein et al. |
| 4,657,638 | A | 4/1987 | le Grand et al. |
| 4,892,938 | A | 1/1990 | Giovanetto |
| 4,917,916 | A | 4/1990 | Hirao et al. |
| 5,112,610 | A | 5/1992 | Kienle |
| 5,576,042 | A | 11/1996 | Fuisz |
| 5,779,805 | A | 7/1998 | Morano |
| 5,962,678 | A | 10/1999 | Payzant et al. |
| 5,972,120 | A | 10/1999 | Kutowy et al. |
| 6,031,157 | A | 2/2000 | Morita et al. |
| 6,080,561 | A | 6/2000 | Morita et al. |
| 6,204,377 | B1 | 3/2001 | Nishimoto et al. |
| 6,228,996 | B1 | 5/2001 | Zhou et al. |
| 6,706,304 | B1 | 3/2004 | Ishida et al. |
| 7,807,206 | B2 | 10/2010 | Magomet et al. |
| 7,838,044 | B2 | 11/2010 | Abelyan et al. |
| 7,862,845 | B2 | 1/2011 | Magomet et al. |
| 8,257,948 | B1 | 9/2012 | Markosyan |
| 2002/0132320 | A1 | 9/2002 | Wang et al. |
| 2003/0161876 | A1 | 8/2003 | Hansson et al. |
| 2003/0232118 | A1* | 12/2003 | Lerchenfeld et al. ........ 426/599 |
| 2003/0236399 | A1 | 12/2003 | Zheng et al. |
| 2006/0083838 | A1 | 4/2006 | Jackson et al. |
| 2006/0134292 | A1 | 6/2006 | Abelyan et al. |

(Continued)

FOREIGN PATENT DOCUMENTS

| BR | P10701736 | | 7/2008 | |
| CN | 1049666 | | 3/1991 | |
| CN | 1100727 | | 3/1995 | |
| CN | 1112565 | | 11/1995 | |
| CN | 1192447 | | 9/1998 | |
| CN | 1238341 | | 12/1999 | |
| CN | 1349997 | | 5/2002 | |
| CN | 101200480 | | 6/2008 | |
| CN | 200910069624 | * | 7/2009 | |
| CN | 101591365 B | * | 12/2011 | ............. A23L 27/10 |
| JP | 52005800 | | 1/1977 | |

(Continued)

OTHER PUBLICATIONS

Hartel, Richard "Crystallization in Foods" Handbook of Industrial Crystallization Elsevier 2002, pp. 287 and 293-296.*

(Continued)

*Primary Examiner* — Kelly Bekker
(74) *Attorney, Agent, or Firm* — Briggs and Morgan, P.A.; Audrey J. Babcock

(57) ABSTRACT

A method for making a highly soluble *Stevia* sweetener is described. The resulting sweetener readily provides solutions with up to or greater than 30% concentration which are stable for more than 24 hours.

6 Claims, No Drawings

(56) References Cited

U.S. PATENT DOCUMENTS

| | | |
|---|---|---|
| 2006/0142555 A1* | 6/2006 | Jonnala et al. .............. 536/18.1 |
| 2007/0082102 A1 | 4/2007 | Magomet et al. |
| 2007/0082103 A1 | 4/2007 | Magomet et al. |
| 2007/0116800 A1 | 5/2007 | Prakash |
| 2007/0116819 A1 | 5/2007 | Prakash |
| 2007/0116820 A1 | 5/2007 | Prakash |
| 2007/0116821 A1 | 5/2007 | Prakash |
| 2007/0116822 A1 | 5/2007 | Prakash |
| 2007/0116823 A1 | 5/2007 | Prakash |
| 2007/0116824 A1 | 5/2007 | Prakash |
| 2007/0116825 A1 | 5/2007 | Prakash |
| 2007/0116826 A1 | 5/2007 | Prakash |
| 2007/0116827 A1 | 5/2007 | Prakash |
| 2007/0116828 A1 | 5/2007 | Prakash |
| 2007/0116829 A1 | 5/2007 | Prakash |
| 2007/0116830 A1 | 5/2007 | Prakash |
| 2007/0116831 A1 | 5/2007 | Prakash |
| 2007/0116832 A1 | 5/2007 | Prakash |
| 2007/0116833 A1 | 5/2007 | Prakash |
| 2007/0116834 A1 | 5/2007 | Prakash |
| 2007/0116835 A1 | 5/2007 | Prakash |
| 2007/0116836 A1 | 5/2007 | Prakash |
| 2007/0116837 A1 | 5/2007 | Prakash |
| 2007/0116838 A1 | 5/2007 | Prakash |
| 2007/0116839 A1 | 5/2007 | Prakash |
| 2007/0116840 A1 | 5/2007 | Prakash |
| 2007/0116841 A1 | 5/2007 | Prakash |
| 2007/0128311 A1 | 6/2007 | Prakash |
| 2007/0134390 A1 | 6/2007 | Prakash |
| 2007/0134391 A1 | 6/2007 | Prakash |
| 2007/0224321 A1 | 9/2007 | Prakash |
| 2007/0292582 A1 | 12/2007 | Prakash et al. |
| 2008/0064063 A1 | 3/2008 | Brandle et al. |
| 2008/0102497 A1 | 5/2008 | Wong et al. |
| 2008/0107775 A1 | 5/2008 | Prakash |
| 2008/0107776 A1 | 5/2008 | Prakash |
| 2008/0107787 A1 | 5/2008 | Prakash |
| 2008/0108710 A1 | 5/2008 | Prakash |
| 2008/0111269 A1 | 5/2008 | Politi et al. |
| 2008/0226797 A1 | 9/2008 | Lee et al. |
| 2008/0292764 A1* | 11/2008 | Prakash et al. .............. 426/548 |
| 2008/0292765 A1 | 11/2008 | Prakash |
| 2008/0292775 A1* | 11/2008 | Prakash et al. .............. 426/658 |
| 2008/0300402 A1 | 12/2008 | Yang et al. |
| 2009/0017185 A1 | 1/2009 | Catani |
| 2009/0053378 A1 | 2/2009 | Prakash |
| 2009/0074935 A1 | 3/2009 | Lee |
| 2009/0079935 A1 | 3/2009 | Harris et al. |
| 2009/0142817 A1 | 6/2009 | Norman et al. |
| 2009/0226590 A1 | 9/2009 | Fouache et al. |
| 2010/0055752 A1 | 3/2010 | Kumar |
| 2010/0056472 A1 | 3/2010 | Duan et al. |
| 2010/0099857 A1 | 4/2010 | Evans et al. |
| 2010/0057024 A1 | 5/2010 | Cavallini et al. |
| 2010/0112159 A1 | 5/2010 | Abelyan et al. |
| 2010/0120710 A1 | 5/2010 | Watanabe et al. |
| 2010/0137569 A1 | 6/2010 | Prakash et al. |
| 2010/0189861 A1 | 7/2010 | Abelyan et al. |
| 2010/0227034 A1 | 9/2010 | Purkayastha et al. |
| 2010/0255171 A1 | 10/2010 | Purkayastha et al. |
| 2010/0278993 A1 | 11/2010 | Prakash et al. |
| 2010/0316782 A1 | 12/2010 | Shi et al. |
| 2011/0030457 A1 | 2/2011 | Valery et al. |
| 2011/0033525 A1 | 2/2011 | Lui |
| 2011/0092684 A1 | 4/2011 | Abelyan et al. |
| 2011/0104353 A1 | 5/2011 | Lee |
| 2011/0111115 A1 | 5/2011 | Shi et al. |
| 2011/0124587 A1 | 5/2011 | Jackson et al. |
| 2011/0160311 A1 | 6/2011 | Prakash et al. |
| 2011/0189360 A1 | 8/2011 | Yoo et al. |
| 2011/0195169 A1 | 8/2011 | Markosyan et al. |
| 2012/0164678 A1 | 6/2012 | Stephanopoulos et al. |
| 2012/0214752 A1 | 8/2012 | Markosyan |

FOREIGN PATENT DOCUMENTS

| | | |
|---|---|---|
| JP | 52083731 | 7/1977 |
| JP | 52100500 | 8/1977 |
| JP | 52136200 | 11/1977 |
| JP | 54030199 | 3/1979 |
| JP | 54132599 | 10/1979 |
| JP | 55039731 | 3/1980 |
| JP | 55081567 | 6/1980 |
| JP | 55092400 | 7/1980 |
| JP | 55120770 | 9/1980 |
| JP | 55138372 | 10/1980 |
| JP | 55159770 | 12/1980 |
| JP | 55162953 | 12/1980 |
| JP | 56099768 | 8/1981 |
| JP | 56109568 | 8/1981 |
| JP | 56121453 | 9/1981 |
| JP | 56121454 | 9/1981 |
| JP | 56121455 | 9/1981 |
| JP | 56160962 | 12/1981 |
| JP | 57002656 | 1/1982 |
| JP | 57005663 | 1/1982 |
| JP | 57046998 | 3/1982 |
| JP | 57075992 | 5/1982 |
| JP | 57086264 | 5/1982 |
| JP | 58020170 | 2/1983 |
| JP | 58028246 | 2/1983 |
| JP | 58028247 | 2/1983 |
| JP | 58212759 | 12/1983 |
| JP | 58212760 | 12/1983 |
| JP | 59045848 | 3/1984 |
| JP | 62166861 | 7/1988 |
| JP | 63173531 | 7/1988 |
| JP | 1131191 | 5/1989 |
| JP | 3262458 | 11/1991 |
| JP | 6007108 | 1/1994 |
| JP | 6192283 | 7/1994 |
| JP | 7143860 | 6/1995 |
| JP | 7177862 | 7/1995 |
| JP | 8000214 | 1/1996 |
| JP | 9107913 | 4/1997 |
| JP | 2000236842 | 9/2000 |
| JP | 2002262822 | 9/2002 |
| JP | 2010516764 | 5/2010 |
| KR | 20070067199 | 6/2007 |
| KR | 20080071605 | 8/2008 |
| KR | 20090021386 | 3/2009 |
| RU | 2111969 | 5/1998 |
| RU | 2123267 | 12/1998 |
| RU | 2156083 | 9/2000 |
| RU | 2167544 | 5/2001 |
| RU | 2198548 | 2/2003 |
| WO | 2005089483 | 9/2005 |
| WO | 2006072878 | 7/2006 |
| WO | 2006072879 | 7/2006 |
| WO | 2008091547 | 7/2008 |
| WO | 2009108680 | 9/2009 |
| WO | 2010118218 | 10/2010 |
| WO | 2011059954 | 5/2011 |
| WO | 2011153378 | 12/2011 |
| WO | 2012082493 | 6/2012 |
| WO | 2012082677 | 6/2012 |
| WO | 2013022989 | 2/2013 |

OTHER PUBLICATIONS

Shi, et al., "Synthesis of bifunctional polymeric adsorbent and its application in purification of Stevia glycosides", Reactive & Functional Polymers, vol. 50 2002, 107-116.

Shibata et al., "Glucosylation of Steviol and Steviol-Glucosides in Extracts from Stevia rebaudiana Bertoni," Plant Physiol. vol. 95, (1991) 152-156.

Starratt, et al., "Rebaudioside F, a diterpene glycoside from Stevia Rebaudiana", Phytochemistry, vol. 59 2002 , 367-370.

Sweet Green Fields, LLC, "Notice to the U.S. Food and Drug Administration (FDA) that the use of Rebiana (Rebaudiosid A) derived from Stevia rebaudiana, as a Food Ingredient is Generally Recognized as Safe (GRAS)," Jan. 15, 2009, http:/www.accessdata.

(56) References Cited

OTHER PUBLICATIONS fda.gov/scripts/fcn/gras_notices/grn000282.pdf (obtained from the WEB on May 8, 2012) entire document esp. p. 22, Table 1, pp. 1-97.
Tanaka, O. , "Improvement of taste of natural sweeteners", Pure & Appl. Chem., vol. 69, No. 4 1997 , 675-683.
Teo, et al., "Validation of green-solvent extraction combined with chromatographic chemical fingerprint to evaluate quality of Stevia rebaudiana Bertoni", J. Sep. Sci, vol. 32 2009 , 613-622.
United Nations' Food and Agriculture Organization/Joint Expert Committee on Food Additives (2010) Steviol Glycosides, Compendium of Food Additive Specifications, FAO JECFA Monographs 10, 17-21.
van der Maarel et al., "Properties and applications of starch-converting enzymes of the a-amylase family," Journal of Biotechnology, vol. 94 (2002) 137-155.
Vasquez, Stimulation of the Gerbil's Gustatory Receptors by Some Potently Sweet Terpenoids, J. Agric. Food Chem., vol. 41, 1305-1310, 1993.
Yamamoto, K. et al., "Effective Production of Glycosyl-steviosides by a-1,6 Transglucosylation of Dextrin Dextranase", Biosci. Biotech. Biochem. vol. 58, No. 9 1994 , 1657-1661.
Yoda, et al., "Supercritical fluid extraction from Stevia rebaudiana Bertoni using CO2 and CO2+ water: extraction kinetics and identification of extracted components", Journal of Food Engineering, vol. 57 2003 , 125-134.
Zell, et al., "Investigation of Polymorphism in Aspartame and Neotame Using Solid-State NMR Spectroscopy", Tetrahedron, vol. 56, 2000, 6603-6616.
Zhang, et al., "Membrane-based separation scheme for processing sweetener from Stevia leaves", Food Research International, vol. 33 2000 , 617-620.
a-Glucosyltransferase Treated Stevia, Japan's Specifications and Standards for Food Additives, VIII edition, 2009, p. 257.
Ahmed, et al., "Use of p-Bromophenacyl Bromide to Enhance Ultraviolet Detection of Water-Soluble Organic Acids (Steviolbioside and Rebaudioside B) in High-Performance Liquid Chromatographic Analysis", Journal of Chromatography, vol. 192, 1980, 387-393.
Chang, S. S. et al., "Stability Studies of Stevioside and Rebaudioside A in Carbonated Beverages", Journal of Agricultural and Food Chemistry, vol. 31, 1983, 409-412.
Chen, et al., "Enrichment and separation of rebaudioside A from stevia glycosides by a novel adsorbent with pyridyl group", Science in China, vol. 42, No. 3 1999 , 277-282.
Chen, et al., "Selectivity of polymer adsorbent in adsorptive separations of stevia diterpene glycisides", Science in China, vol. 41, No. 4 1998 , 436-441.
Chen, et al., "Studies on the adsorptive selectivity of the polar resin with carbonyl group on rebaudioside A", Acta Polymeric Scnica, No. 4 1999 , 398-403.
Crammer, et al., "Sweet glycosides from the Stevia plant", Chemistry in Britain, Oct. 1986, 915-916, 918, considered only as disclosed.
Darise et al., "Enzymic Transglucosylation of Rubusoside and the Structure-Sweetness Relationship of Steviol Bisglycosides," Agric. Biol. Chem. vol. 48(10), 1984, 2483-2488.
Dubois et al., "Diterpenoid Sweeteners. Synthesis and Sensory Evaluation of Stevioside Analogues with Improved Organoleptic Properties," J. Med. Chem. vol. 28, (1985) 93-98.
Fuh, , "Purification of steviosides by membrane and ion exchange process", Journal of Food Science, vol. 55, No. 5 1990 , 1454-1457.
Fukunaga et al., "Enzymic Transglucosylation Products of Stevioside: Separation and Sweetness-evaluation," Agric. Biol. Chem. vol. 53(6) (1989) 1603-1607.
Fullas et al., "Separation of natural product sweetening agents using overpressured layer chromatography," Journal of Chromatography vol. 464 (1989) 213-219.
Hale, et al., "Amylase of Bacillus Macerans", Cereal Chemistry, vol. 28, No. 1, Jan. 1951, 49-58.

International Search Report and Written Opinion of PCT/US2010/055960, pp. 1-11 mailed Jan. 2011.
International Search Report and Written Opinion of PCT/US2011/028028, pp. 1-8, mailed May 2011.
International Search Report and Written Opinion of PCT/US2011/033734, pp. 1-8, mailed Jul. 2011.
International Search Report and Written Opinion of PCT/US2011/033737, pp. 1-8, mailed Jul. 2011.
International Search Report and Written Opinion of PCT/US2011/033912, pp. 1-6, mailed Jul. 2011.
International Search Report and Written Opinion of PCT/US2011/035173, pp. 1-7, mailed Aug. 2011.
International Search Report and Written Opinion of PCT/US2011/036063, mailed Aug. 5, 2011, pp. 1-7, mailed Aug. 2011.
International Search Report and Written Opinion of PCT/US2011/047498, mailed Dec. 22, 2011, pp. 1-8.
International Search Report and Written Opinion of PCT/US2011/047499, mailed Dec. 22, 2011, pp. 1-8.
International Search Report and Written Opinion of PCT/US2011/064343, pp. 1-17, mailed Jan. 2, 2013.
International Search Report and Written Opinion of PCT/US2012/024585, pp. 1-8. mailed Jun. 2012.
International Search Report and Written Opinion of PCT/US2012/024722, pp. 1-8, mailed May 2012.
International Search Report and Written Opinion of PCT/US2012/030210, pp. 1-10 mailed Jul. 2012.
International Search Report and Written Opinion of PCT/US2012/043294, pp. 1-7, mailed Sep. 2012.
International Search Report and Written Opinion of PCT/US2012/051163, pp. 1-9 mailed Oct. 2012.
International Search Report and Written Opinion of PCT/US2012/052659, pp. 1-9, mailed Nov. 2012.
International Search Report and Written Opinion of PCT/US2012/052665, pp. 1-8, mailed Nov. 2012.
International Search Report and Written Opinion of PCT/US2013/030439, pp. 1-10, mailed May 2013.
Jaitak, et al., "An Efficient Microwave-assisted Extraction Process of Stevioside and Rebaudioside-A from Stevia Rebaudiana (Bertoni)", Phytochem. Anal. vol. 20 2009 , 240-245.
Kennelly, "Sweet and non-sweet constituents of Stevia rebaudiana", Stevia: The genus *Stevia*, Taylor & Francis, 2002, 68-85.
Kinghorn, "Overview", Stevia: The genus *Stevia*, Taylor & Francis, 2002, 1-17.
Kitahata, S. et al., "Production of Rubusoside Derivatives by Transgalactosylation of Various b-Galactosidases", Agric. Biol. Chem., vol. 53, No. 11 1989 , 2923-2928.
Kobayashi, et al., "Dulcoside A and B, New diterpene glycosides from Stevia Rebaudiana", Phytochemistry, vol. 16 1977 , 1405-1408.
Kochikyan, et al., "Combined Enzymatic Modification of Stevioside and Rebaudioside A", Applied Biochemistry and Microbiology, vol. 42, No. 1, 2006, 31-37.
Kohda, et al., "New sweet diterpene glucosides from Stevia Rebaudiana", Phytochemistry, vol. 15 1976 , 981-983.
Kovylyaeva, et al., "Glycosides from Stevia rebaudiana", Chemistry of Natural Compounds, vol. 43, No. 1 2007 , 81-85.
Liu, et al., "Study of stevioside preparation by membrane separation process", Desalination, vol. 83 1991 , 375-382.
Lobov, S. V. et al., "Enzymic Production of Sweet Stevioside Derivatives: Transglucosylation of Glucosidases", Agric. Biol. Chem., vol. 55, No. 12 1991 , 2959-2965.
Montovaneli, et al., "The effect of temperature and flow rate on the clarification of the aqueous Stevia-extract in fixed-bed column with zeolites", Brazilian Journal of Chemical Engineering, vol. 21, No. 3 2004 , 449-458.
Moraes, et al., "Clarification of Stevia rebaudiana (Bert.) Bertoni extract adsorption in modified zeolites", Acta Scientiarum, vol. 23, No. 6 2001 , 1375-1380.
Ohta et al., "Characterization of Novel Steviol Glycosides from Leaves of Stevia rebaudiana Morita," J. Appl. Glycosi., vol. 57, 199-209, 2010.

(56) References Cited

OTHER PUBLICATIONS

Ohtani et al. "Chapter 7. Methods to improve the taste of the sweet principles of Stevia rebaudiana." The Genus *Stevia*, edited by A. Douglas Kinghorn, CRC Press 2001, Taylor and Francis, London and New York, pp. 138-159.

Phillips, K. C. , "Stevia: steps in developing a new sweetener", in T.H. Grenby, Editor, Developments in Sweeteners-3, Elsevier 1987 , 1-43.

Pol, et al., "Comparison of two different solvents employed for pressurised fluid extraction of stevioside from Stevia rebaudiana: methanol versus water", Anal Bioanal Chem vol. 388 2007 , 1847-1857.

Prakash et al., "Development of rebiana, a natural, non-caloric sweetener," Jul. 1, 2008, Food and Chemical Toxology, vol. 46, Is. 7, Sup. 1, p. S75-S82.

Richman et al., "Fuctional genomics uncovers three glucosyltransferases involved in the synthesis of the major sweet glucosides of Stevia rebaudiana," The Plant Journal, vol. 41 (2005) 56-67.

Sakamoto et al., "Application of 13C NMR Spectroscopy to Chemistry of Natural Glycosides: Rebaudioside-C, a New Sweet Diterpene Glycoside of Stevia Rebaudiana", Chem. Pharm. Bull., vol. 25, 1977, 844-846.

* cited by examiner

HIGHLY SOLUBLE STEVIA SWEETENER

FIELD OF THE INVENTION

The invention relates to a process for the preparation of highly soluble individual or combined sweet glycosides from a *Stevia rebaudiana* Bertoni plant extract, and more particularly for preparation of highly soluble rebaudioside A.

DESCRIPTION OF THE RELATED ART

It is well known that Rebaudioside A exhibits so called polymorphism (Zell et al., 2000). Rebaudioside A amorphous, anhydrous and solvate forms differ significantly from each other in terms of solubility which is one of the main criteria for the commercial viability of a sweetener. In this regard, as shown in Table 1, the hydrate form of Rebaudioside A displays the lowest solubility (Prakash et al., 2008). It was shown that Rebaudioside A may transform from one polymorph form to another at certain conditions (U.S. patent application Ser. No. 11/556,049).

TABLE 1

Properties of Rebaudioside A forms (U.S. patent application Ser. No. 11/556,049)

| | Polymorph Forms | | | |
| --- | --- | --- | --- | --- |
| | Form 1 Hydrate | Form 2 Anhydrous | Form 3 Solvate | Form 4 Amorphous |
| Rate of dissolution in $H_2O$ at 25° C. | Very low (<0.2% in 60 minutes) | Intermediate (<30% in 5 minutes) | High (>30% in 5 minutes) | High (>35% in 5 minutes) |
| Alcohol content | <0.5% | <1% | 1-3% | <0.05% |
| Moisture content | >5% | <1% | <3% | 6.74% |

Patent application WO/2010/118218 describes a process of producing highly soluble rebaudioside A by preparing a highly soluble hydrated crystalline form. However the described methodology utilizes low throughput techniques such as evaporative crystallization or hot filtration/centrifugation of slurries which can be hard to accomplish in large industrial scale.

On the other hand it is known (Prakash et al., 2008) that rebaudioside A amorphous forms prepared by spray drying display high solubility as well. However spray drying of rebaudioside A is a very challenging and low throughput task because generally spray drying requires concentrated feed solutions (about 50% solids content). Rebaudioside A concentrated solutions prepared by simple dissolution are very unstable and tend to crystallize very fast. These concentrated solutions (>10%) prepared by common solubilization methods such as heating under normal conditions crystallize shortly after cooling down to room temperature. Thus spray drying of such solutions requires special equipment capable of maintaining the solution at elevated temperature.

On the other hand extended exposure of rebaudioside A to high temperature both in solid form and in aqueous solutions results in hydrolytic decomposition of the material (Prakash et al., 2008).

Therefore a high throughput process of manufacturing highly soluble Rebaudioside A or other steviol glycosides on an industrial scale without needing a sophisticated equipment setup will offer certain advantages compared to other techniques known to art.

SUMMARY OF THE INVENTION

The invention is directed to a method for producing a sweetener comprising the steps of providing a *Stevia* sweetener powder and solubilizing it in the water under gradient temperature treatment conditions, to produce a highly stable concentrated solution, and spray drying the highly stable concentrated solution to obtain a highly soluble *Stevia* sweetener powder.

Hereinafter the term "steviol glycoside(s)" will mean Rebaudioside A, Rebaudioside B, Rebaudioside C, Rebaudioside D, Rebaudioside E, Rebaudioside F, Stevioside, Steviolbioside, Dulcoside A, Rubusoside, or other glycoside of steviol and combinations thereof.

Hereinafter, unless specified otherwise, the solubility of material is determined in RO (reverse osmosis) water at room temperature. Where the solubility is expressed as "%" it to be understood as number of grams of material soluble in 100 grams of solvent.

It is to be understood that both the foregoing general description and the following detailed description are exemplary and explanatory and are intended to provide further explanation of the invention as claimed.

DETAILED DESCRIPTION OF THE INVENTION

A process for the preparation of highly soluble *Stevia* sweetener, particularly Rebaudioside A, is described herein.

Crystalline Rebaudioside A has an inherently very low solubility, ranging from about 1%-2%. As described above, Rebaudioside A exhibits polymorphism, resulting in a variety of forms with very different characteristics and handling properties. The hydrate form has very low solubility (less than 0.2%), and is therefore not commercially viable as a sweetener. The solvate form has a solubility typically greater than 30%, but this form has only of scientific interest and cannot be used for food or beverage applications because the level of residual alcohol (1-3%) makes it unfit for use in foods and beverages. The anhydrous form has a solubility reported in literature of a maximum of up to about 30% solubility. The amorphous form has as solubility generally greater than 30%, but for its preparation, the crystalline form has to be dissolved in the water at very high concentrations (approx, 50%) which is not achievable by common solubilization techniques.

Typical spray drying techniques involve the use of a highly concentrated, and yet stable, starting solution to achieve the highest output possible. As noted above, crystalline Rebaudioside A has a very low solubility, so to create a stable solution (one which will not crystallize at room temperature), the solution has to be very dilute. Spray drying very dilute solutions is not economically efficient as the output of the spray dried powder will be very low. The need exists, therefore, for a process in which a high solubility Rebaudioside A is obtained by a process which does not require significantly diluted Rebaudioside A solution in order for the solution to be stable at room temperature.

In one embodiment of the present invention, an initial material, comprising sweet glycoside(s) of the *Stevia rehauthana* Bertoni plant extract, which includes Stevioside, Rebaudioside A, Rebaudioside B, Rebaudioside C, Rebaudioside D, Rebaudioside E, Rebaudioside F, Steviolbioside, Duicoside A, Ruhusoside or other glycoside of steviol and combinations thereof, was combined with water at a ratio of about 1:1 (w/w).

The obtained mixture was further subjected to a gradient heat treatment which resulted in high stability and high concentration solution. The gradient of about 1° C. per minute was used in heating the mixture. The mixture was heated to the temperature of about 110-140° C., preferably about 118-125° C. and was held at maximum temperature for about 0-120 min, preferably about 50-70 min.

After the heat treatment the solution was cooled down to room temperature at gradient of about about 1° C. per minute, 24-hour incubation of this high stability and high concentration solution did not show any crystallization.

The solution was spray dried by a laboratory spray drier operating at about 175° C. inlet temperature and about 100° C. outlet temperature. A highly soluble amorphous form of rebaudioside A was obtained with greater than about 30% solubility in water at room temperature.

The following examples illustrate preferred embodiments of the invention. It will be understood that the invention is not limited to the materials, proportions, conditions and procedures set forth in the examples, which are only illustrative.

Example 1

Preparation of Rebaudioside A Concentrated Solution 100 g of rebaudioside A containing Stevioside 0.2%, Rebaudioside C 0.3%, Rebaudioside F 0.3%, Rebaudioside A 97.7%, Rebaudioside D 1.0%, and Rebaudioside B 0.3%, all percentages being on a percent dry weight basis, and having water solubility of 0.6% was mixed with 100 g of water and boiled on a laboratory heater until complete dissolution. Upon complete dissolution, the solution was cooled to room temperature to make Solution #1.

Example 2

Preparation of Rebaudioside A Concentrated Solution 100 g of rebaudioside A containing Stevioside 0.2%, Rebaudioside C 0.3%, Rebaudioside F 0.3%, Rebaudioside A 97.7%, Rebaudioside D 1.0%, Rebaudioside B 0.3%, all percentages being on a percent dry weight basis, and having water solubility of 0.6% was mixed with 100 g of water and incubated in autoclave (AMA 270, Astell Scientific, UK), at 12° C. for 1 hour. Upon completion of incubation period the obtained clear solution was cooled to room temperature to make Solution #2.

Example 3

Preparation of Rebaudioside A Concentrated Solution 100 g of rebaudioside A containing Stevioside 0.2%, Rehaudioside C 0.3%, Rebaudioside F 0.3%, Rehaudioside A 97.7%, Rebaudioside D 1.0%, Rebaudioside B 0.3%, all percentages being on a percent dry weight basis, and having water solubility of 0.6% was mixed with 100 g of water and incubated in thermostatted oil bath. The temperature was increased at 1° C. per minute to 121° C. The mixture was maintained at 121° C. for 1 hour and then the temperature was decreased to room temperature (2.5° C.) at 1° C. per minute to make Solution #3.

Example 4

Rebaudioside A Concentrated Solution Stability

Rebaudioside A Solution 41, Solution #2 and Solution #3 prepared according to EXAMPLE 1, EXAMPLE 2 and EXAMPLE 3, respectively, were assessed in terms of their stability at room temperature (25° C.). The results are summarized in Table 2.

TABLE 2

Rebaudioside A concentrated solution stability (50% total solids, 25° C.)

| Time, hrs | Solution #1 | Solution #2 | Solution #3 |
|---|---|---|---|
| 0.5 | Clear solution | Clear solution | Clear solution |
| 1 | Intensive crystallization | Cloudy solution, precipitate on the bottom | Clear solution |
| 2 | Viscous slurry of crystals | Intensive crystallization | Clear solution |
| 4 | Solidified crystalline mixture | Viscous slurry of crystals | Clear solution |
| 24 | Solidified crystalline mixture | Solidified crystalline mixture | Clear solution |

It can be seen that the solution prepared by temperature gradient method shows greater stability against crystallization.

Example 5

Preparation of Highly Soluble Rebaudioside A

Rebaudioside A Solution #1, Solution #2 and Solution #3 prepared according to EXAMPLE 1, EXAMPLE 2 and EXAMPLE 3, respectively, were dried using YC-015 laboratory spray drier (Shanghai Pilotech Instrument & Equipment Co. Ltd., China) operating at 175° C. inlet and 100° C. outlet temperature. Solution #1 and Solution #2 had to be maintained at 80° C. to prevent premature crystallization whereas Solution #3 was maintained at room temperature. The Solution #1 yielded Sample #1, Solution #2 yielded Sample #2 and Solution #3 yielded Sample #3.

The obtained amorphous powder samples were compared for solubility (Table 3).

TABLE 3

Highly soluble Rebaudioside A

| Solubility, % | Observation | | |
|---|---|---|---|
| | Sample #1 | Sample #2 | Sample #3 |
| 5 | Clear solution | Clear solution | Clear solution |
| 10 | Slightly cloudy solution | Clear solution | Clear solution |
| 20 | Cloudy solution | Slightly cloudy solution | Clear solution |

TABLE 3-continued

Highly soluble Rebaudioside A

| Solubility, % | Observation | | |
|---|---|---|---|
| | Sample #1 | Sample #2 | Sample #3 |
| 30 | Undissolved matter on the bottom | Cloudy solution | Clear solution |
| 40 | Significant amount of undissolved matter | Significant amount of undissolved matter | Slightly cloudy solution |

The process of the present invention resulted in a Rebaudioside A polymorph which demonstrated high degree of solubility in water. Although the foregoing embodiments describe the use of Rebaudioside A, it is to be understood that any *Stevia*-based sweetener may be used and prepared in accordance with this invention, and all *Stevia*-based sweeteners are contemplated to be within the scope of the present invention.

Although the invention and its advantages have been described in detail, it should be understood that various changes, substitutions and alterations can be made herein without departing from the spirit and scope of the invention as defined by the appended claims. Moreover, the scope of the application is not intended to be limited to the particular embodiments of the invention described in the specification. As one of ordinary skill in the art will readily appreciate from the disclosure of the invention, the compositions, processes, methods, and steps, presently existing or later to be developed that perform substantially the same function or achieve substantially the same result as the corresponding embodiments described herein may be utilized according to the invention.

I claim:

1. A method for producing a highly soluble sweetener consisting of the steps of:

A) providing a *Stevia* sweetener powder;
B) providing a solvent consisting essentially of water;
C) mixing the solvent and *Stevia* sweetener powder to make a mixture;
D) increasing the temperature of the mixture by a gradient heat treatment method having a rate of temperature change of about 1° C. per minute to an elevated temperature of about 110-140° C. to make a solution;
E) holding the solution at the elevated temperature;
F) decreasing the temperature of the solution by a gradient cooling method having a regular rate of temperature change to obtain a stable *Stevia* sweetener solution having a clear solution stability without visible crystallization or cloudiness at 25° C. for 24 hours; and
G) optionally spray drying the stable *Stevia* sweetener solution, to provide an amorphous highly soluble powder of *Stevia* sweetener having a solubility of at least about 5 grams per 100 grams of water.

2. The method of claim 1 wherein *Stevia* sweetener is selected from a group consisting of: Stevioside, Rebaudioside A, Rebaudioside B, Rebaudioside C, Rebaudioside D, Rebaudioside E, Rebaudioside F, Steviolbioside, Dulcoside A, Rubusoside, or other glycoside of steviol, and a mixture thereof.

3. The method of claim 1 wherein the water and *Stevia* sweetener powder ratio in the mixture is 1:1 (w/w).

4. The method of claim 1 wherein the decreasing of the temperature of the solution is at a gradient of about 1° C. per minute.

5. The method of claim 1 wherein the solution is held at 110-140° C. for about 50-70 minutes.

6. The method of claim 1 wherein the stable *Stevia* sweetener solution is spray dried on a spray drying apparatus operating at 175° C. inlet and 100° C. outlet temperature.

* * * * *